(12) United States Patent
Vlasic

(10) Patent No.: US 10,675,169 B2
(45) Date of Patent: Jun. 9, 2020

(54) ANKLE FOOT ORTHOSIS

(71) Applicant: aNImaKe d.o.o., Maribor (SI)

(72) Inventor: Matej Vlasic, Maribor (SI)

(73) Assignee: aNImaKe d.o.o., Maribor (SI)

( * ) Notice: Subject to any disclaimer, the term of this patent is extended or adjusted under 35 U.S.C. 154(b) by 235 days.

(21) Appl. No.: 15/841,977

(22) Filed: Dec. 14, 2017

(65) Prior Publication Data

US 2018/0177624 A1    Jun. 28, 2018

(30) Foreign Application Priority Data

Dec. 27, 2016  (SI) .................... P-201600312

(51) Int. Cl.
| | |
|---|---|
| *A61F 5/01* | (2006.01) |
| *A43B 7/20* | (2006.01) |
| *A43D 1/02* | (2006.01) |
| *A43B 7/14* | (2006.01) |
| *A61B 5/107* | (2006.01) |
| *A61B 5/103* | (2006.01) |
| *A61B 5/00* | (2006.01) |

(52) U.S. Cl.
CPC ............ *A61F 5/0127* (2013.01); *A43B 7/141* (2013.01); *A43B 7/20* (2013.01); *A43D 1/022* (2013.01); *A43D 1/025* (2013.01); *A61F 5/0111* (2013.01); *A61B 5/1036* (2013.01); *A61B 5/1071* (2013.01); *A61B 5/1073* (2013.01); *A61B 5/4595* (2013.01); *A61F 5/0195* (2013.01)

(58) Field of Classification Search
CPC ..... A61B 5/1071; A61F 5/0111; A61F 5/0127
See application file for complete search history.

(56) References Cited

U.S. PATENT DOCUMENTS

| | | | |
|---|---|---|---|
| 10,528,032 B2 * | 1/2020 | Schouwenburg | .... A61B 5/4851 |
| 2018/0353308 A1 * | 12/2018 | Tompkins | ................ A61F 2/50 |

FOREIGN PATENT DOCUMENTS

| | | |
|---|---|---|
| WO | 2006053283 A2 | 5/2006 |
| WO | 2009139019 A1 | 11/2009 |

* cited by examiner

*Primary Examiner* — James Sanders
(74) *Attorney, Agent, or Firm* — The Watson IP Group, PLC; Jovan N. Jovanovic

(57) ABSTRACT

The ankle foot orthosis solves a problem of a poor adaptation to a user's foot (3) and the related discomfort. It provides for simultaneous correction of several symptoms in the foot and ankle areas. It is completely produced from a uniform material, the thickness and shape of which change depending on user's specific needs. It is designed in such a way that it does not intervene with other functions of a user's foot. It is manufactured by preparing a 3D model of a user's foot when placed in a physiologically correct static position, by modelling the ankle foot orthosis directly to a 3D model of the foot (3), by 3D printing from preferably a photopolymer, and by adequate post-processing. Due to its minimalistic design, the user can wear the orthosis in a shoe of his appropriate foot size.

7 Claims, 3 Drawing Sheets

ANKLE FOOT ORTHOSIS

CROSS-REFERENCE TO RELATED APPLICATION

This application claims priority from Slovenian Patent Application Number P-201600312 entitled "ANKLE FOOT ORTHOSIS", filed Dec. 27, 2016, the entire disclosure of which is hereby incorporated by reference in its entirety.

BACKGROUND

The object of the invention is an ankle foot orthosis and a method for the manufacturing thereof, which is completely adapted to a user's foot. It is preferably produced from a photopolymer by using a 3D printer and can simultaneously address various symptoms.

There are several solutions in the field of manufacturing ankle foot orthoses. A development of new technologies and materials has opened new possibilities. An innovative application of new tools for capturing, processing and producing, offers a possibility for the manufacturing of an ankle foot orthosis having the features which were not possible with the existing technologies.

Several solutions to the manufacturing of an ankle foot orthosis adapted to an individual user are used in practice; however, they do not achieve an optimal effect as different methods and materials than those described in this claim are used. Ankle foot orthoses are most frequently made from plastics and can be inserted into a shoe having a somewhat bigger size than a shoe that would be otherwise suitable for a user. Some orthoses also consist of several parts and are inserted into a specially customized shoe. All these solutions share a common point, namely that their function is normally focused on the treatment or alleviation of one symptom, while an integral treatment of a foot is not taken into consideration.

The invention belongs to class A61F 5/00 of the international classification.

Patent application WO/2006/053283 describes an ankle foot orthosis that consists of several parts and is intended to stabilise the ankle and to contribute to more natural walking. Its adaptation to the user is not optimal, it is manufactured more generically and the solution is therefore impractical and uncomfortable to use.

The ankle foot orthosis from patent application WO/2009/139019 is formed of an elastic band that is wound around a foot and the area below the knee. It is exclusively meant to correct supination and pronation of a user's foot. The use of elastic materials alleviates symptoms to a certain extent, but fails to completely hold the foot in a proper position.

SUMMARY OF THE DISCLOSURE

It is common to all mentioned and known solutions that they are not optimally adapted to an individual user and only address single symptoms. A problem that remains unsolved due to the use of conventional technological solutions is solving several symptoms simultaneously, constructional over-dimension and inadaptation to an individual user. The latter causes various skin damages such as blisters, callus, abrasions and all these cause discomfort.

The technical problem solved by the invention is such a process of capturing data, processing and manufacturing an ankle foot orthosis, that allows the orthosis to completely fit a user's foot and such shape of an ankle foot orthosis that will allow selective correction of individual symptoms and several symptoms simultaneously and will at the same time not reduce other user's functionalities such as flexibility.

BRIEF DESCRIPTION OF THE DRAWINGS

The invention refers to both, to an ankle foot orthosis and to a method of manufacturing thereof.

The problem of the invention is solved by an individual approach to the user; from 3D scanning of a foot shape, data processing, modelling, and manufacturing of an ankle foot orthosis. All this makes it possible to eliminate all mentioned problems. The invention and the method of the invention will be described by way of an embodiment and drawings, in which.

DETAILED DESCRIPTION OF THE DRAWINGS

Figure 2:
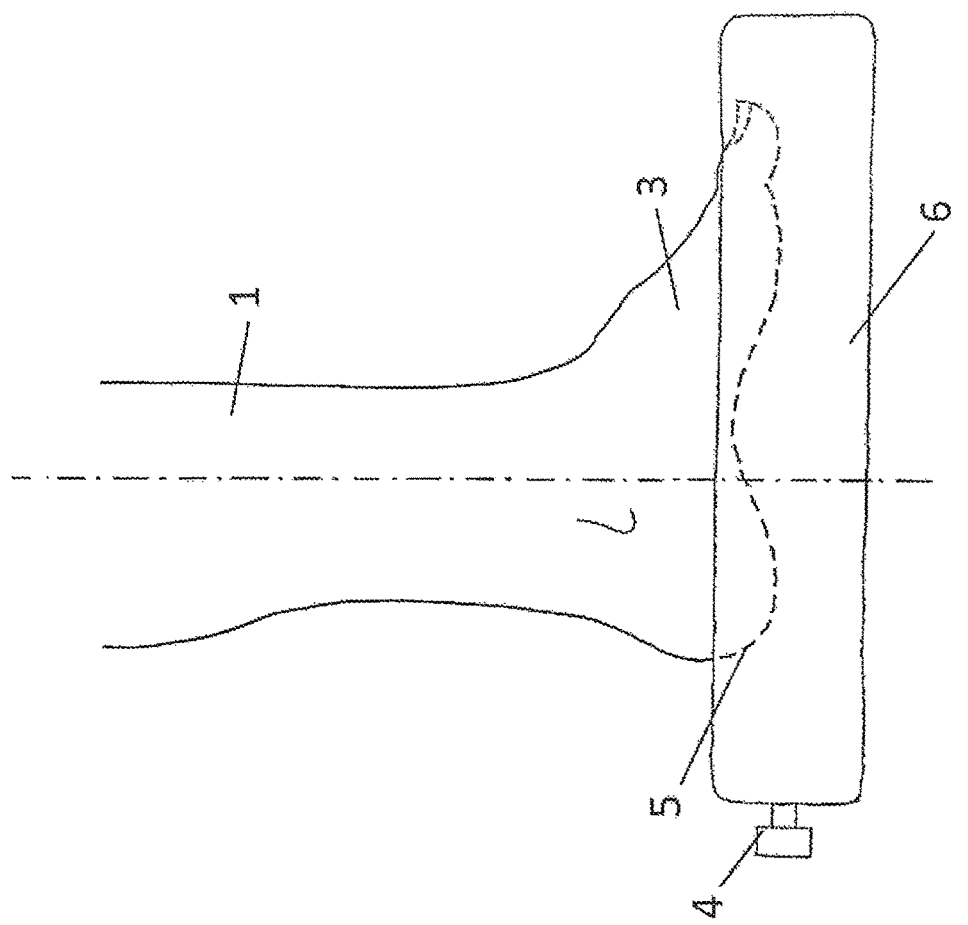
FIG. 2 shows a side view of a user's foot positioned in a physiologically correct static position.
Figure 1:
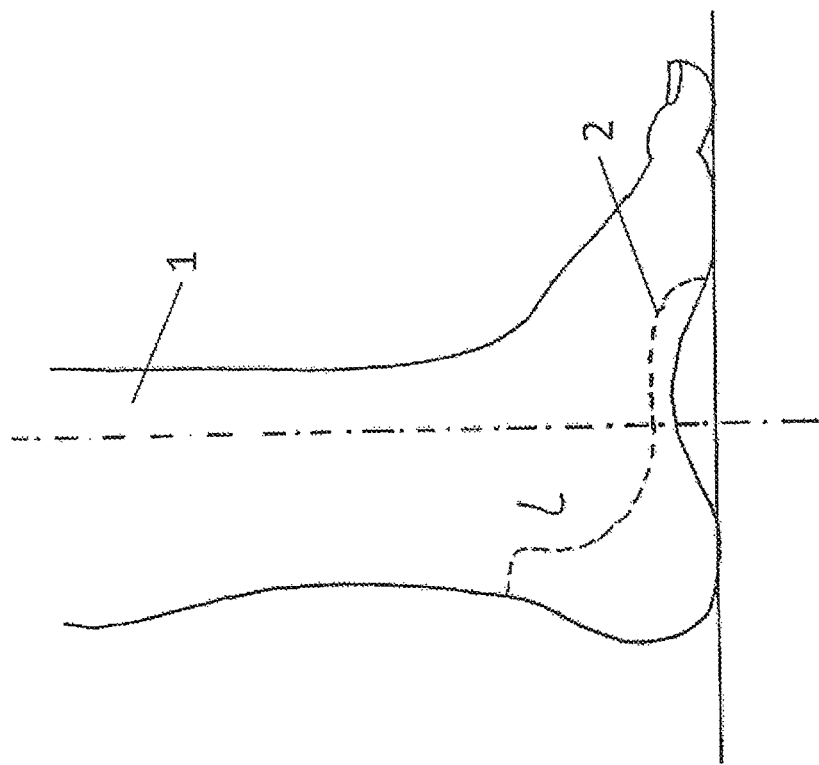
FIG. 1 shows a side view of a user's foot and boundaries of an ankle foot orthosis.
Figure 4:
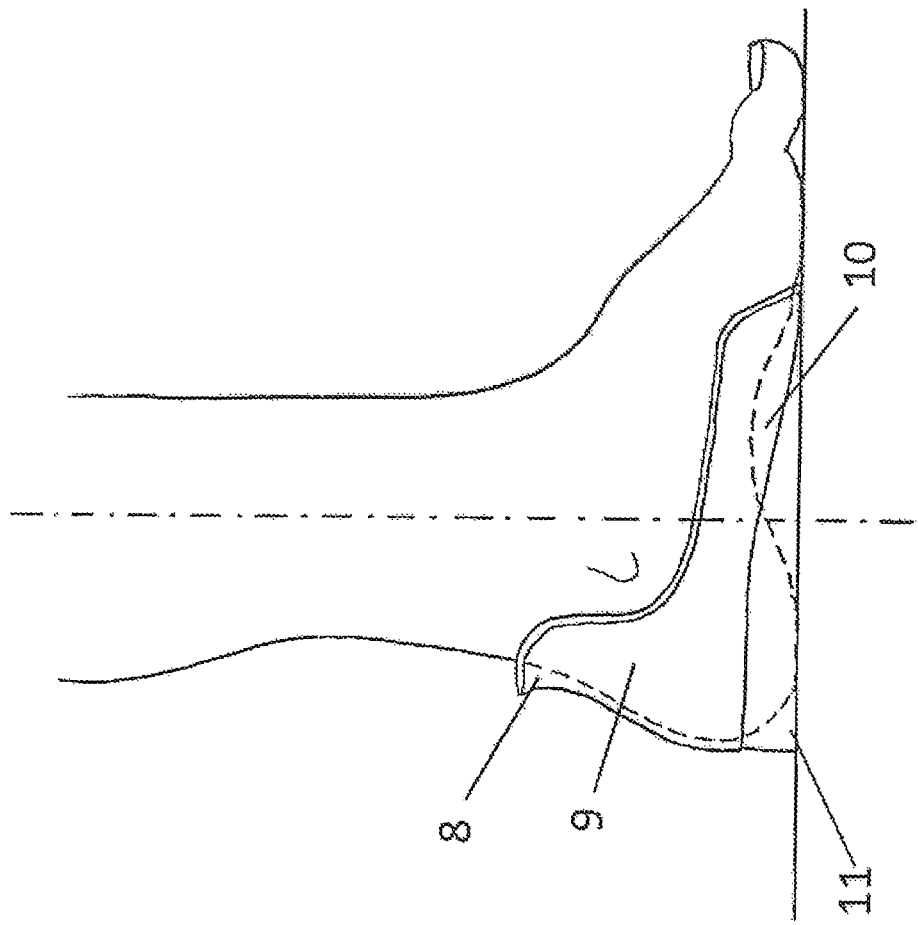
FIG. 4 shows a side view of the ankle foot orthosis with a user's foot.
Figure 3:
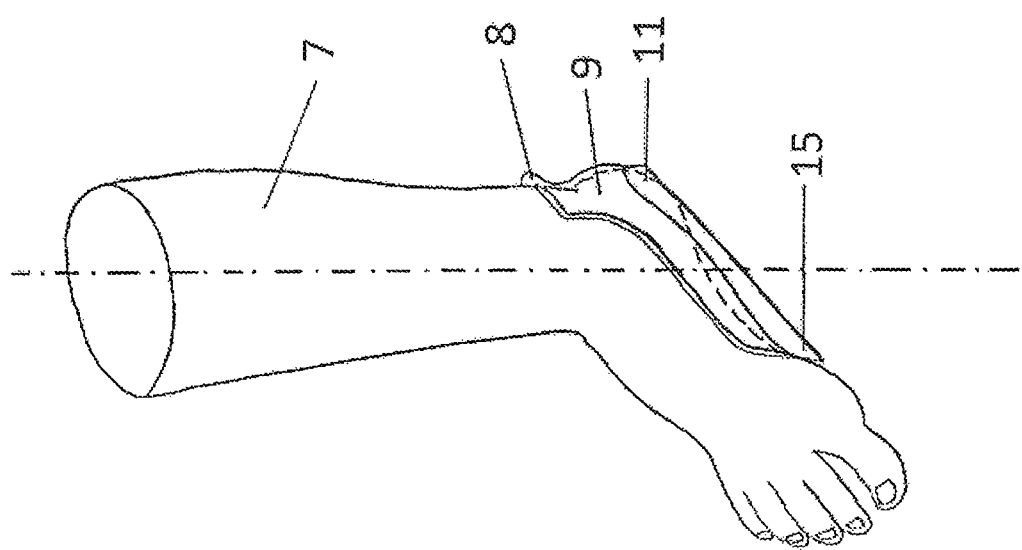
FIG. 3 shows the ankle foot orthosis with a user's foot in 3D projection.
Figure 6:
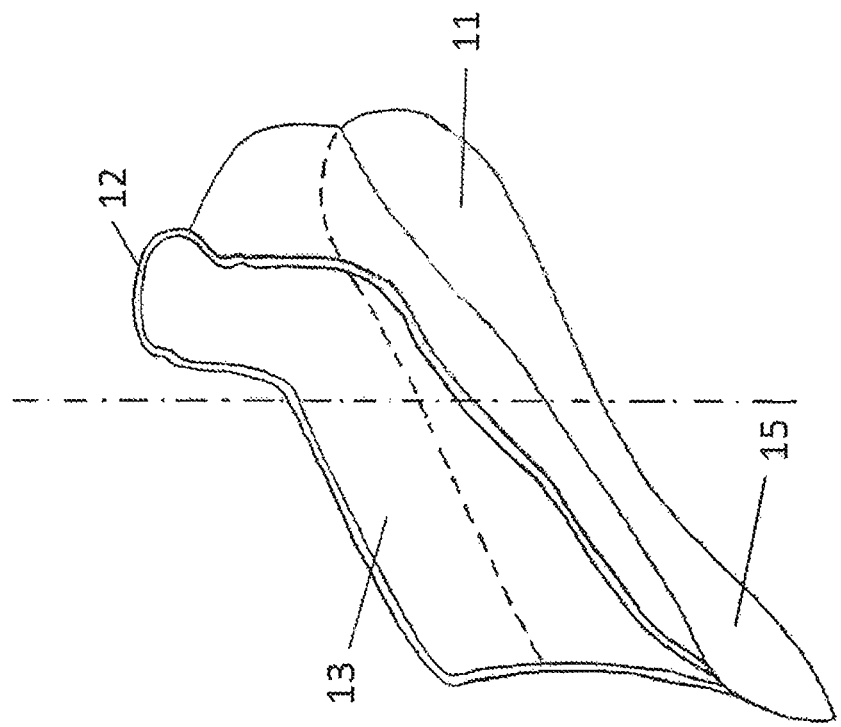
FIG. 6 shows a view of the ankle foot orthosis in 3D projection.
Figure 5:
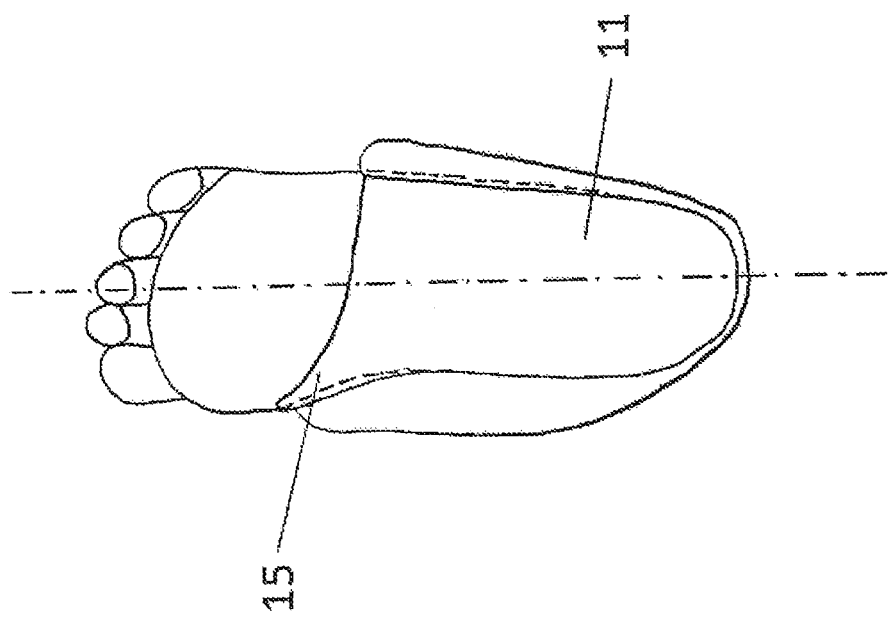
FIG. 5 shows a bottom view of the ankle foot orthosis with a user's foot.

The ankle foot orthosis described in this invention is useful for a user having lower central muscular tone, hyper elastic joints and consequently overturned foot arch and tilted heel bone. It also proves beneficial in spastic muscles of lower extremities, which results in too much support on the front part of the foot, which shows as walking on toes, and also results on too much weight on the inner part of the foot. The ankle foot orthosis described in the embodiment sets the foot into a physiologically correct static position thus having influence on the entire stance or statics of the body. The ankle foot orthosis of the invention is modelled in a way to include an expressed foot arch 10, a lateral support 12, a support 9 in the ankle section which conveys a feeling of stability in case of centrally low muscular tone, an end portion 15 on the edge of the foot arch 10, an end portion 8 on the Achilles tendon, which slightly presses against it at every step and thus slowly extends it, which is beneficial in the alleviation of symptoms of spastic muscles, and a stabilising flat section 11. Due to its optimised design the ankle foot orthosis is used in a shoe of a suitable size for a user's foot. This means that the orthosis is designed in a way to only fill in the empty space in a shoe of a suitable size for a user's foot. A sock is always used between the ankle foot orthosis and a user's foot.

The ankle foot orthosis of the invention is shaped as to user's symptoms, wherein a minimalistic approach is always taken into consideration. This means that the ankle foot orthosis of the invention encloses only that part of the foot surface necessary for treatment of the user's symptoms. The ankle foot orthosis is preferably produced from a single piece of a uniform plastic mass. The current prior art ankle foot orthoses always enclose the entire foot surface, i.e. the entire surface of the sole of the foot, regardless of the symptoms and their stage, and extend at the back almost to the knee fold. A user therefore gets too thick and too high orthoses which impact the mobility and what's more, the use of such an ankle foot orthosis requires shoes which are for 2 to 3 numbers larger than shoes than would be normally suitable for the user's foot. With the use of the minimalistic approach in manufacturing ankle foot orthoses by 3D printing, the ankle foot orthosis of the invention completely fits a user's foot and can be used in a shoe that is of a suitable size for the user's foot.

In few cases a part of an ankle foot orthosis which lays in the area of the dorsum of the foot and/or the tibia needs to be added, wherein individual constituent parts of the ankle foot orthosis can be joined by appropriate belts which allow setting the force, with which various parts of the ankle foot orthosis are fastened. A reason why the ankle foot orthosis is to be manufactured from several parts is the above-mentioned minimalistic approach. In such cases, if an ankle foot orthosis would be manufactured from one piece, this would increase its size when complex symptoms are treated and this would be disturbing for the function of a foot and user's comfort.

The innovative technology of 3D printing by photopolymerization is used for the manufacturing of the ankle foot orthosis of the invention. Currently the vacuum-molded thermo plastics are used for the manufacturing of ankle foot orthoses, where a heated plate from a synthetic polymer is pressed against a foot mould in the vacuumization process. In this technology, excess material is cut off. Instead of removing the material in the technology currently applied, the technology of the invention makes it possible to apply material layer by layer and a single piece ankle foot orthosis is thus manufactured.

Thanks to the innovative approach, in which a user's foot 3 is captured with a 3D scanner, the ankle foot orthosis is configured in compliance with personal symptoms focused primarily on these areas. The ankle foot orthosis of the invention eliminates the symptoms of the shortened Achilles tendon, pronation, plantarflexion and ankle instability, wherein it individually alleviates various symptoms or several different symptoms simultaneously.

Due to the applied technology of 3D scanning, the ankle foot orthosis of the invention allows manufacturing of an orthosis which completely fits a user's foot. Modelling of an ankle foot orthosis is carried out directly to a 3D model of a foot 3, which means that no extra space is left between the ankle foot orthosis and the 3D model, wherewith the movement of the foot 3 inside the ankle foot orthosis, which would otherwise cause various skin damages as described above, is eliminated. Since during the 3D scanning the foot 3 is set into a physiologically correct static position under the user's weight, there is a reduced risk for discomfort. Well-planned modelling of the ankle foot orthosis pays attention to adding material to the areas which contribute to the treatment of symptoms and to a more comfortable use.

To the ankle foot orthosis described in the present invention a stabilizing flat portion 11 is added that can be, depending on the user's symptoms, parallel to the ground or forced dorsiflexion of the foot or plantar flexion of the foot at an angle specific for user's needs is recommended; this means that in the event of a shortened Achilles tendon and consequently toe walking, the flat section 11 is manufactured at an angle which forces the user into dorsiflexion of the foot 3, while in the event when the user's centre of gravity is primarily on a heel, the stabilising flat section 11 is produced at an angle which forces the user to plantar flexion of the foot 3. With its minimalistic shape said ankle foot orthosis has been developed with an aim to be used in commercially available unadjusted shoes for various purposes and in suitable sizes with regard to a user's foot.

The support 9 in the ankle area tightly fits the ankle and prevents, due to its adequate height, uncontrolled ankle movements. It therefore provides stabilisation of the ankle area and thus enables a better feeling while walking. The height of the ankle foot orthosis in the ankle area is defined on the basis of user's symptoms: when the user has a very increased muscle tonus in the foot 3, the ankle foot orthosis in the ankle area at the back along the Achilles tendon can reach up to a height which already allows setting the foot 3 in a proper position.

The ankle foot orthosis described in the present invention has a shaped lateral support 12 and the support 9 in the ankle area, wherein the thickness of the supports is adapted to specific user's symptoms and his weight and is not necessarily identical in all needed stabilisation areas. A principle of minimisation is used here.

The lateral support 12 and the support 9 in the ankle area provide for adequate constructional stability of the ankle foot orthosis, while the stabilizing flat section 11 provides for its static stability.

The ankle foot orthosis described in the invention has a specially shaped end portion 8 in the area of the Achilles tendon, which does not reduce the flexibility of the ankle but slightly presses against the tendon during every step. In the event of symptoms with spastic muscles, a user has his Achilles tendon stretched to such an extent that it forces him to walk on toes. This end portion 8 allows for additional stimulation and relaxation of this area during walking.

The ankle foot orthosis described in this invention has an expressed foot arch 10, with which it offers support to this area. The symptoms of pronation and clubfoot 3 are herewith alleviated. The adequate foot arch 10 is defined each time when the foot 3 is positioned to a proper position during 3D scanning of the foot 3 and is adapted to user's symptoms. The foot arch 10 can be supported in all positions up to the ideal placement of the foot 3, wherein user's feelings and comfort are taken into consideration. This symptom can thus be gradually corrected. The corrected foot arch 10 has a great impact on the physiologically proper position of the body and user's stance while walking.

On the edge of the foot arch 10 the ankle foot orthosis described in this invention has a shaped end portion 15 which serves for gradual reduction of the height of the foot arch 10 to the ground and allows the user to comfortably use the ankle foot orthosis without experiencing any skin damages in this area. The end portion 15 needs to end in front of the big toe bone in order not to trigger the Grasp primitive reflex.

1. The method for manufacturing the ankle foot orthosis described in this invention is carried out in the following phases:

2. Placement of the foot 3 into a physiologically correct static position

3. Digital capturing of the shape with a 3D scanner

4. Data processing and modelling of the ankle foot orthosis

5. Preparation of a 3D model of the ankle foot orthosis for the method of 3D printing 6. 3D printing 7 Post-processing Phase 1: A user's foot 3, preferably in an upright position, is inserted into a special silicone bag 6 filled with micro beads and having a pneumatic attachment 4. A vacuum pump is connected to this attachment and the air is suctioned out of the bag 6. When there is no more air in the bag, the latter can be freely shaped. By pressing on the surface of the silicone bag, the micro beads are pushed away from an area where they are not needed to an area, in which they must offer support to the foot thus placing it to a physiologically correct static position. A different synthetic mass can be used for this step, which allows modelling to such an extent that the user's foot 3 is maintained in the physiologically correct static position and preserves this shape also when the user does no longer press against it with his weight and the foot 3.

Phase 2: By using a 3D scanner, the visible portion of the user's foot 3 from the toes to the knee is captured when the user is in the standing position. The user then steps out of the bag 6, in which the imprint 5 of the foot 3 remained and this is also captured by the 3D scanner. The data obtained in this way are captured in a 3D digital mesh.

Phase 3: In the programme for 3D processing of meshes the captured data are joined to one whole, i.e. the user's foot 3 in the physiologically correct static position. Depending on the specific user's symptoms, the programme is first used to draw the outer boundary 2 of the ankle foot orthosis directly to the 3D model of the foot 3. The latter is then modelled in the programme in order to correct the symptoms. The ankle foot orthosis is then exported from the programme in a 3D form suitable for being used in a 3D printer.

Phase 4: In the programme for the preparation for 3D printing, the ankle foot orthosis is positioned such that a static surface 13 between the ankle foot orthosis and the user's foot 3 remains intact during the 3D printing process. It is well-known from the technique of 3D printing that the method of photopolymerization is carried out in layers, wherein the layers are planned in a way that they are supported by a special support structure or provide themselves with sufficient support during the 3D printing process itself. The contact surface 13 should not contain specific structures dedicated to the success of the printing process itself, since they impact the smoothness of the surface and consequently the user's comfort.

Phase 5: To manufacture the ankle foot orthosis described in this invention, a 3D printer is used with the precision which allows manufacturing of a smooth contact surface 13 with the user's foot 3 without subsequent post-processing, wherewith the discomfort in wearing the orthosis is prevented. The preferably used material is a photopolymer but other synthetic masses can also be used. The ankle foot orthosis is preferably produced with a precision of at least 0.1 mm.

Phase 6: In the manufacturing process during the photopolymerization process, support structures can be manufactured on the external part of the ankle foot orthosis for constructional stability reasons. These support structures need to be adequately removed and the rough structure eliminated. Depending on the photopolymer used and compliant with the instructions for the material used the obtained ankle foot orthosis needs to be additionally irradiated with a light of suitable wavelength for a certain period of time in order to achieve a suitable mechanical properties of the material used.

The invention claimed is:

1. A method of manufacturing an ankle foot orthosis adapted to an individual user's symptoms to be treated, said method comprising:
   placing a user's foot into a physiologically correct static position;
   digitally capturing a shape of the foot with a 3D scanner;
   data modelling of the ankle foot orthosis based on the digital capture of the shape of the foot;
   preparing a 3D model of the ankle foot orthosis for 3D printing based on the modelling of the ankle foot orthosis;
   3D printing the ankle foot orthosis with a 3D printer;
   placing the user's foot in the physiologically correct static position onto a silicone pillow filled with a synthetic mass;
   modelling said synthetic mass and the user's foot placed in the physiologically correct static position;
   joining a mesh of a visible portion of the user's foot from toes of the user to a knee of the user and a mesh of an imprint of the shape of the user's foot, the joined mesh defining the user's foot in the physiologically correct static position; and
   depending on specific symptoms of the user, first drawing directly to the 3D model of the foot an outer boundary of the ankle foot orthosis, prior to the 3D printing of the ankle foot orthosis;
   wherein said ankle foot orthosis is modelled directly to the captured 3D model of the user's foot and fits the user's foot for selective correction of at least one of an individual symptom of the user and several symptoms of the user, simultaneously; and
   wherein said synthetic mass preserves the imprint of the shape of the user's foot placed into a physiologically correct static position also when the user no longer presses against said synthetic mass with a user's weight and the foot.

2. The method of manufacturing according to claim 1, further comprising:
   capturing in a 3D digital mesh, by the 3D scanner, including a visible portion of the user's foot from toes of the user to a knee of the user while the user is standing of a pillow with the foot placed into the physiologically correct static position.

3. The method of manufacturing according to claim 1, wherein the digital capture of the shape of the foot is captured in a 3D digital mesh.

4. The method of manufacturing according to claim 1, further comprising:
   positioning the ankle foot orthosis such that a contact surface between the ankle foot orthosis and the user's foot remains intact during the 3D printing.

5. The method of manufacturing according to claim 1, wherein the 3D printer has a precision of at least 0.1 mm to manufacture a smooth contact surface between the ankle foot orthosis and the user's foot.

6. The method of manufacturing according to claim 1, further comprising:
   post-processing including removing support structures manufactured on an external part of the ankle foot orthosis for constructional stability reasons, during a photopolymerization process.

7. The method of manufacturing according to claim 1, wherein the ankle foot orthosis eliminates the symptoms of at least one of a shortened Achilles tendon, pronation, plantarflexion, and ankle instability.

* * * * *